(12) United States Patent
Yamaoka et al.

(10) Patent No.: US 10,351,600 B2
(45) Date of Patent: Jul. 16, 2019

(54) PEPTIDE AND COMPLEX OF SAME, SCAFFOLD FOR TISSUE REPAIR AND SURFACE TREATMENT METHOD FOR SAME, AND SURFACE TREATMENT SOLUTION OR SET OF TREATMENT SOLUTIONS

(71) Applicants: NATIONAL CEREBRAL AND CARDIOVASCULAR CENTER, Suita-shi, Osaka (JP); JMS Co., Ltd., Hiroshima-shi, Hiroshima (JP)

(72) Inventors: Tetsuji Yamaoka, Suita (JP); Sachiro Kakinoki, Suita (JP); Shunsuke Baba, Osaka (JP); Yoshiya Hashimoto, Osaka (JP)

(73) Assignees: National Cerebral and Cardiovascular Center, Suita-shi, Osaka (JP); JMS Co., Ltd., Hiroshima-shi, Hiroshima (JP)

( * ) Notice: Subject to any disclaimer, the term of this patent is extended or adjusted under 35 U.S.C. 154(b) by 0 days.

(21) Appl. No.: 15/663,043

(22) Filed: Jul. 28, 2017

(65) Prior Publication Data

US 2017/0327539 A1 Nov. 16, 2017

Related U.S. Application Data

(62) Division of application No. 14/787,228, filed as application No. PCT/JP2014/061771 on Apr. 25, 2014, now abandoned.

(30) Foreign Application Priority Data

Apr. 26, 2013 (JP) ................. 2013-094744

(51) Int. Cl.
| | | |
|---|---|---|
| *C07K 9/00* | (2006.01) | |
| *C07K 7/08* | (2006.01) | |
| *A61L 27/54* | (2006.01) | |
| *A61L 27/12* | (2006.01) | |
| *A61L 27/58* | (2006.01) | |
| *C07K 14/50* | (2006.01) | |

(52) U.S. Cl.
CPC ............... *C07K 7/08* (2013.01); *A61L 27/12* (2013.01); *A61L 27/54* (2013.01); *A61L 27/58* (2013.01); *C07K 9/00* (2013.01); *C07K 14/50* (2013.01); *A61L 2300/236* (2013.01); *A61L 2300/25* (2013.01); *A61L 2300/414* (2013.01)

(58) Field of Classification Search
None
See application file for complete search history.

(56) References Cited

U.S. PATENT DOCUMENTS

| | | | |
|---|---|---|---|
| 5,866,402 A | 2/1999 | Innis et al. | |
| 2004/0141945 A1 | 7/2004 | Yura et al. | |
| 2005/0288398 A1 | 12/2005 | Messersmith et al. | |
| 2008/0255046 A1 | 10/2008 | Schwartz et al. | |
| 2009/0018642 A1 | 1/2009 | Benco | |
| 2011/0033891 A1* | 2/2011 | Cha ................. | C07K 14/43504 435/69.1 |

FOREIGN PATENT DOCUMENTS

| | | |
|---|---|---|
| CN | 1042162 A | 5/1990 |
| CN | 1989152 A | 6/2007 |
| CN | 101065134 A | 10/2007 |
| CN | 101111273 A | 1/2008 |
| JP | H02-191629 | 7/1990 |
| JP | 11-511117 | 9/1999 |
| JP | 2008-504016 | 2/2008 |
| JP | 2010-521246 | 6/2010 |
| JP | 2012-016517 | 1/2012 |
| WO | WO 02/081619 A1 | 10/2002 |
| WO | WO 2005/092920 A1 | 10/2005 |
| WO | WO 2012067837 A1 | 5/2012 |

OTHER PUBLICATIONS

Mikolasch, Annett et al., "Laccase-catalyzed cross-linking of amino acids and peptides with dihydroxylated aromatic compounds", Springer-Verlag 2010, Amino Acids (2010) 39: pp. 671-683.
Search Report dated Nov. 24, 2016 in corresponding European Patent Application No. 14788321.9.
Papst Stefanie, et al., "Synthesis and SAR of a Library of Cell-Permeable Biotin-$R_8$ERY* Peptidomimetics Inhibiting $\alpha 4\beta 7$ Integrin Mediated Adhesion of TK-1 Cells to MAdCAM-1-Fc". Australian Journal of Chemistry, 2012, 65, pp. 1349-1358.
Waite, "Ahesion a la Moule", Integr Comp. Biol., 2002, pp. 1172-1180.
Waite et al., "Polyphosphoprotein from the Adhesive Pds of Mytilus edulis", Biochemistry, 2001, pp. 2887.2893.

* cited by examiner

*Primary Examiner* — Lianko G Garyu
(74) *Attorney, Agent, or Firm* — Muncy, Geissler, Olds & Lowe, P.C.

(57) ABSTRACT

A peptide that enables surface treatment of a scaffold for tissue repair that makes it possible to accelerate the repair of living tissue without using a material that negatively affects the repair of living tissue, a complex containing this peptide, a scaffold for tissue repair surface treated using this peptide or this complex, a surface treatment method for a scaffold for tissue repair using this peptide or this complex, and a treatment solution or set of treatment solutions to be used in this surface treatment method. Surface treatment of a scaffold for tissue repair is conducted by combining glycosaminoglycan and a peptide containing adhesive sites and basic sites each comprising predetermined amino acid residues.

8 Claims, 7 Drawing Sheets
Specification includes a Sequence Listing.

(Top: HE stained; Bottom: anti-CD31 antibody immunostained)

PEPTIDE AND COMPLEX OF SAME, SCAFFOLD FOR TISSUE REPAIR AND SURFACE TREATMENT METHOD FOR SAME, AND SURFACE TREATMENT SOLUTION OR SET OF TREATMENT SOLUTIONS

CROSS-REFERENCE TO RELATED APPLICATIONS

This application is a Divisional of co-pending application Ser. No. 14/787,228 filed on Oct. 26, 2015, which is a U.S. National Stage of International Application No. PCT/JP2014/061771 filed on Apr. 25, 2014, for which priority is claimed under 35 U.S.C. § 120; and this application claims priority of Application No. 2013-094744 filed in Japan on Apr. 26, 2013 under 35 U.S.C. § 119; the entire contents of all of which are hereby incorporated by reference.

TECHNICAL FIELD

The present invention relates to a peptide ideally used in the surface treatment of scaffold for tissue repair, and a complex containing this peptide. In addition, the present invention relates to a scaffold for tissue repair that is surface treated using this peptide or this complex. Furthermore, the present invention relates to a surface treatment method of a scaffold for tissue repair using this peptide or this complex, and a treatment solution or set of treatment solutions for surface treatment of a scaffold for tissue repair containing this peptide or this complex.

BACKGROUND ART

Conventionally, a material that is called scaffold serving as the foundation of cell growth has been used in the repair of various living tissues. As the materials of such a scaffold, natural or synthetic polymers, and inorganic materials have been variously used; however, the compatibility between these materials and living tissues is not necessarily high. For this reason, even if a scaffold is applied to the repair of living tissues, the tissue may not be repaired to the desired extent, or considerable time may be required in the repair of tissue.

In order to solve such problems, it has been known to use scaffold along with cell growth factor. As the material for living tissue repair using a scaffold along with cell growth factor, for example, an osteoanagenesis material containing cell growth factor such as fibroblast growth factor (FGF) has been known (refer to Patent Document 1).

Patent Document 1: Japanese Unexamined Patent Application, Publication No. 2012-016517

DISCLOSURE OF THE INVENTION

Problems to be Solved by the Invention

However, even when using by simply physically mixing the scaffold and cell growth factor as described in Patent Document 1, the cell growth factor may separate from the scaffold while repairing the tissue, and thus the desired promotion effect on tissue repair is hardly obtained. In order to prevent separation of the cell growth factor from the scaffold, it has been considered to fix the cell growth factor to the scaffold by way of chemical cross-linkers or electro-static interactions. However, with such a method, not only are structural deformation of the cell growth factor and an activity decline of concern, but also the negative influence on the repair of living tissue induced by the materials used in fixation is also of concern.

The present invention has been made by taking the above-mentioned problems into account, and has an object of providing a peptide that enables the surface treatment of a scaffold for tissue repair that can promote the repair of living tissue without using a material that negatively influences the repair of living tissue, a complex containing this peptide, a scaffold for tissue repair that has been surface treated using this peptide or this complex, a surface treatment method of scaffold for tissue repair using this peptide or this complex, and a treatment solution or set of treatment solutions to be used in this surface treatment method.

Means for Solving the Problems

The present inventors have discovered that the above-mentioned problems could be solved by performing surface treatment of scaffold for tissue repair by combining a peptide including an adhesive site and basic site, each consisting of predetermined amino acid residues, and glycosaminoglycan, thereby arriving a completion of the present invention. More specifically, the present invention provides the followings.

(1) A peptide comprising, in the amino acid sequence thereof, an adhesive site consisting of residues of amino acids including a 2,3-dihydroxyphenyl group or 3,4-dihydroxyphenyl group, and a basic site including three or more consecutive basic amino acid residues.

(2) The peptide according to (1), wherein the adhesive site and the basic site bind via a spacer site.

(3) The peptide according to (1) or (2) wherein N terminus or C terminus is a basic terminus that includes a basic site at the terminus or vicinity thereof, and
wherein a site in which an amino acid residue is not present, or consisting of at least 1 to no more than 5 amino acid residues and not including the adhesive site is present on a basic terminus side from the basic site.

(4) The peptide according to (3), wherein another end relative to the basic terminus is an adhesive terminus having an adhesive site at a terminus or vicinity thereof, and
wherein the adhesive site is contained and the basic site is not contained within five amino acid residues from the adhesive terminus.

(5) The peptide according to (4), wherein a sequence of nine resides from the C terminus is an amino acid sequence represented by SEQ ID NO 1.

(6) A complex comprising the peptide according to any one of (1) to (5) and glycosaminoglycan.

(7) A complex of the peptide according to any one of (1) to (5), glycosaminoglycan and cell growth factor,
wherein the cell growth factor is binding with the glycosaminoglycan, and binding with the adhesive site of the peptide via the glycosaminoglycan.

(8) A scaffold for tissue repair, wherein the peptide according to any one of (1) to (5) is binding to the surface thereof at the adhesive site.

(9) A scaffold for tissue repair having glycosaminoglycan on a surface thereof,
wherein the peptide according to any one of (1) to (5) is binding with the surface of the scaffold at the adhesive site, and
wherein the glycosaminoglycan is binding with the basic site of the peptide.

(10) A scaffold for tissue repair having cell growth factor on a surface thereof, wherein the peptide according to any one of (1) to (5) is binding with the surface of the scaffold at the adhesive site, and wherein the cell growth factor is binding with glycosaminoglycan, and binding with the basic site of the peptide via the glycosaminoglycan.

(11) A surface treatment method of a scaffold for tissue repair, comprising bringing the peptide according to any one of (1) to (5) into contact with a surface of the scaffold for tissue repair.

(12) The surface treatment method of a scaffold for tissue repair according to (11), further comprising binding glycosaminoglycan to the basic site of the peptide.

(13) The surface treatment method of a scaffold for tissue repair according to (12), further comprising binding cell growth factor to the glycosaminoglycan bound to the peptide.

(14) A surface treatment method of a scaffold for tissue repair, comprising bringing the complex according to (6) into contact with a surface of the scaffold for tissue repair.

(15) The surface treatment method of a scaffold for tissue repair according to (14), further comprising binding cell growth factor to the glycosaminoglycan in the complex.

(16) A surface treatment method of a scaffold for tissue repair, comprising bringing the complex according to (7) into contact with a surface of the scaffold for tissue repair.

(17) A treatment solution for surface treatment of a scaffold for tissue repair, comprising the peptide according to any one of (1) to (5).

(18) A set of treatment solutions for surface treatment of a scaffold for tissue repair, comprising the treatment solution according to (17) and a treatment solution containing glycosaminoglycan.

(19) The set of treatment solutions for surface treatment of a scaffold for tissue repair according to (18), further comprising a treatment solution containing cell growth factor.

(20) A treatment solution for surface treatment of a scaffold for tissue repair, comprising the complex according to (6).

(21) A set of treatment solutions for surface treatment of a scaffold for tissue repair, comprising the treatment solution according to (20) and a treatment solution containing cell growth factor.

(22) A treatment solution for surface treatment of a scaffold for tissue repair, comprising the complex according to (7).

Effects of the Invention

According to the present invention, it is possible to provide: a peptide that enables surface treatment of a scaffold for tissue repair that makes it possible to accelerate the repair of living tissue without using a material that negatively affects the repair of living tissue, a complex containing this peptide, a scaffold for tissue repair surface treated using this peptide or this complex, a surface treatment method for a scaffold for tissue repair using this peptide or this complex, and a treatment solution or set of treatment solutions to be used in this surface treatment method.

PREFERRED MODE FOR CARRYING OUT THE INVENTION

First Embodiment

A peptide according to a first embodiment of the present invention is a peptide having an adhesive site consisting of residues of amino acids including a 2,3-dihydroxyphenyl group or 3,4-dihydroxyphenyl group, and a basic site with at least three consecutive basic amino acid residues in the amino acid sequence. Hereinafter, in the disclosure of the present application, this peptide is also noted as "adhesive peptide". The so-called adhesive peptide can bind with the surface of the scaffold used in tissue repair at the adhesive site, and can bind with glycosaminoglycan at the basic site. Hereinafter, in the disclosure of the present application, the "scaffold for tissue repair" is also simply noted as "scaffold".

The peptide according to the first embodiment is ideally used in the surface treatment of scaffold for tissue repair. The tissue to be repaired using the surface treated scaffold for tissue repair is not particularly limited. As preferred tissue to be repaired using the surface treated scaffold for tissue repair, blood vessels, skin, muscle, cartilage, bone, alimentary canal, breast cardiac valve, periodontal tissue, periocular tissue, and the like can be exemplified.

The number of amino acid residues constituting the peptide according to the first embodiment is not particularly limited in a scope that does not inhibit the objects of the present invention. Typically, the number of amino acid residues constituting the adhesive peptide is preferably at least 4 to no more than 10, more preferably at least 5 to no more than 50, and particularly preferably at least 10 to no more than 30.

The adhesive site possessed by the adhesive peptide consists of residues of amino acid having a 2,3-dihydroxyphenyl group or 3,4-dihydroxyphenyl group. The adhesive site can bind with the surface of the scaffold due to having a dihydroxyphenyl group adjacent to two hydroxyl groups.

In the case of the scaffold consisting of metallic material, the adhesive peptide will bind to the surface of the scaffold via the adhesive site by chelation between the metal atoms present at the surface of the scaffold and the dihydroxylphenyl groups. In the case of the scaffold consisting of a material such as organic polymer or ceramic having functional groups including active hydrogen like hydroxyl groups or amino groups, the adhesive peptide binds to the surface of the scaffold via the adhesive site by the quinone generated by the dihydroxyphenyl group being oxidized and the functional group including active hydrogen like hydroxyl groups and amino groups reacting.

Due to the ease of reaction with the surface of the scaffold by 2,3-dihydrophenyl group and 3,4-dihydroxylphenyl group, 3,4-dihydroxyphenyl group is preferable. As specific examples of amino acids having a 3,4-dihydroxyphenyl group, 3-(3,4-dihydroxyphenyl)-L-alanine(L-dopa), 3-(3,4-dihydroxyphenyl)-2-methyl-L-alanine(methyldopa), (3R)-3-(3,4-dihydroxyphenyl)-L-serine (DOPS), etc. can be exemplified. Among these, 3-(3,4-dihydroxyphenyl)-L-alanine(L-dopa) is preferable due to, in practice, being used as an amino acid constituting peptides in living organisms like *Mytilus coruscus*, being easy to obtain upon preparing peptides, etc.

Although the adhesive peptide binds with glycosaminoglycan at the basic site, the adhesive peptide according to the first embodiment can cause the glycosaminoglycan to bind at the basic site more effectively upon bringing the adhesive peptide and glycosaminoglycan into contact, due to having a basic site with at least three consecutive basic amino acid residues. The number of consecutive residues of the basic amino acids constituting the basic site is preferably at least 3 to no more than 30, and more preferably at least 3 to no more than 10. Other than lysine residue (Lys), arginine residue (Arg) and histidine residue (His), the residues of amino acids constituting the basic site are selected from 5-hydroxylysine, ornithine, kynurenine and modified amino acid residues of these. It should be noted that modification of amino acid residues is not particularly limited so long as the amino acid residue after modification is basic, and can be selected from various known modifications of amino acid residues.

In the adhesive peptide, it is preferable for the adhesive site and basic site to bind through a spacer site. Although the number of amino acid residues constituting the spacer site is not particularly limited, it is preferably at least 1 to no more than 50, and more preferably at least 3 to no more than 30. In the case of the adhesive site and basic site binding via a spacer site constituted from such a number of amino acid residues, since the peptide chain extending from the surface of the scaffold with the adhesive site as the starting point is relatively freely movable, the capture of glycosaminoglycan by the basic site and the capture of cell growth factor by the glycosaminoglycan bound to the basic site are easy.

With the adhesive peptide, it is preferable for the N terminus and C terminus to be a basic terminus including a basic site in the terminus or the vicinity thereof. Including a basic site in the terminus or the vicinity thereof is a situation where a site amino acid residues are not present, or a site consisting of at least 1 to no more than 5 amino acid residues and not including the adhesive site, is present on a side of the basic terminus from this basic site. In the case of a peptide chain so long as to be more on the side of the basic terminus from the basic site being present, it may be difficult to capture the glycosaminoglycan by the basic site due to steric hindrance of the peptide chain more to the side of the basic terminus than the basic site. However, if the basic site is at the terminus of the adhesive peptide or in the vicinity thereof, such a problem will not easily arise.

In addition, it is preferable for the other side of the basic terminus of the adhesive peptide to be an adhesive terminus including an adhesive site in the terminus or the vicinity thereof. Including the adhesive site in the terminus or the vicinity thereof is a state including the adhesive site and not including the basic site within 5 amino acid residues from the adhesive terminus. When the adhesive peptide includes the adhesive terminus, due to being a state where almost the entire length of the adhesive peptide is freely movable at the surface of the scaffold, glycosaminoglycan tends to be captured by the basic terminus.

As the adhesive peptide including such a basic terminus and adhesive terminus, it is preferable for the amino acid sequence of 9 residues from the C terminus to be the amino acid sequence shown by SEQ ID NO. 1 below. The amino acid sequence shown by SEQ ID NO. 1 below is an acid sequence that is repeatedly present in the amino acid sequence of the adhesive peptide produced by *Mytilus coruscus*. The adhesive peptide produced by *Mytilus coruscus* can strongly bind to various substrates due to having a site consisting of such a repeating sequence.

Ala-Lys-Pro-Ser-Tyr-Hyp-Thr-Xaa-Lys　　　(1)

(In SEQ ID NO (1), Xaa is a residue of L-dopa.)

The adhesive peptide can be acquired by way of a known technique following the designed amino acid sequence. As suitable methods, solid-phase synthesis methods such as the Fmoc method and Boc method can be exemplified. The crude adhesive peptide obtained by such solid-phase synthesis methods can be purified using a method such as reverse phase HPLC as necessary. Whether or not the acquired adhesive peptide is the desired sequence can be confirmed by a known means. As such a means, a method that compares between the molecular weight of the adhesive peptide measured by MALDI-TOF/MS and the molecular weight in theory of the adhesive peptide calculated from the amino acid sequence can be exemplified.

The above explained adhesive peptide can bind to the surface of various scaffolds at the adhesive site, and can bind glycosaminoglycan at the basic site. In addition, glycosaminoglycan can being with various cell growth factors. For this reason, after surface treating the scaffold with the adhesive peptide according to the first embodiment, if further surface treated using glycosaminoglycan or glycosaminoglycan and cell growth factor, it is possible to remarkably promote tissue repair by using the scaffold.

Second Embodiment

The second embodiment of the present invention is a complex consisting of the aforementioned adhesive peptide and glycosaminoglycan. With this complex, glycosaminoglycan is binding at the basic site of the adhesive peptide. This complex is formed by mixing the adhesive peptide and glycosaminoglycan in water, for example.

The type of glycosaminoglycan is not particularly limited in a scope not inhibiting the objects of the present invention. As specific examples of the glycosaminoglycan, heparin, heparin sulfate, chondroitin sulfate, dermatan sulfate, keratin sulfate and hyaluronic acid can be exemplified. Among these glycosaminoglycans, heparin is preferable due to obtaining being easy and inexpensive, and excelling in bindability with cell growth factor.

When bringing the complex according to the second embodiment into contact with the surface of the scaffold for tissue repair, the complex binds to the surface of the scaffold at the adhesive site possessed by the adhesive peptide in the complex. The scaffold in which the complex according to the second embodiment is bound to the surface can cause cell growth factor to bind to the glycosaminoglycan included in the complex. For this reason, when placing such a scaffold within the tissue that is the repair target, depending on the type of tissue, it is possible to focus the cell growth factor present within the tissue at the scaffold periphery, and promote repair of tissue.

In addition, it is preferable to bind the cell growth factor to the complex according to the second embodiment supported on the surface of the scaffold in advance. When this is done, it is possible to control release of cell growth factor at the scaffold periphery by placing the scaffold within the tissue to be repaired, and thus the promoting effect on tissue repair can be further enhanced.

The molecular weight of glycosaminoglycan is not particular limited in a scope that does not inhibit the objects of the present invention. Normally, the molecular weight of the glycosaminoglycan is preferably 3,000 to 1,000,000 Daltons, more preferably 3,000 to 100,000 Daltons, and particularly preferably 5,000 to 30,000 Daltons. In the case of using glycosaminoglycan with a molecular weight in such a range, formation of the complex of adhesive peptide, glycosaminoglycan and cell growth factor is easy.

Third Embodiment

The third embodiment of the present invention is a complex of the aforementioned adhesive peptide, glycosaminoglycan and cell growth factor. With this complex, the glycosaminoglycan binds at the basic site of the adhesive peptide, and the cell growth factor binds to the glycosaminoglycan binding to the adhesive peptide. This complex is formed by mixing the adhesive peptide, glycosaminoglycan and cell growth factor in water, for example.

When bringing the complex according to the third embodiment into contact with the surface of the scaffold for tissue repair, the complex binds to the surface of the scaffold at the adhesive site possessed by the adhesive peptide in the complex. When placing the scaffold in which the complex according to the third embodiment is bound to the surface thereof within the tissue that is the repair target, the cell growth factor contained in the complex is control released at the surface of the scaffold, whereby the repair of tissue is remarkably promoted.

The type of cell growth factor is not particularly limited, and is selected as appropriate according to the type of target tissue for repair using the scaffold. As examples of the cell growth factor, epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte colony-stimulating factor (G-CSF), granulocyte-macrophage colony-stimulating factor (GM-CSF), platelet-derived growth factor (PDGF), erythropoietin (EPO), thrombopoietin (TPO), fibroplast growth factor (FGF), bone morphogenetic protein (BMP), interleukin 1 (IL-1), interleukin (IL-2), interferon γ (IFN-γ), tumor necrosis factor α (TNF-α), schwannoma-derived growth factor (SDGF), hepatocyte growth factor (HGF), etc. can be exemplified.

Fourth Embodiment

The fourth embodiment of the present invention is a scaffold for tissue repair in which the aforementioned adhesive peptide is binding to the surface of the scaffold for tissue repair at the adhesive site possessed by the adhesive peptide. The scaffold for tissue repair of the fourth embodiment can further bind glycosaminoglycan due to the adhesive peptide binding to the surface having a basic site, and can bind cell growth factor via the glycosaminoglycan.

The material constituting the scaffold is not particularly limited, and is selected as appropriate from materials used as the material of conventional scaffolds for tissue repair. As the material of the scaffold, natural polymers such as collagen, gelatin, fibrin, alginic acid, cellulose and chitin; synthetic polymers such as polyglycolic acid (PGA), polylactic acid (PLA), polycaprolactone (PCL), polyethylene glycol (PEG), polymethylene carbonate, polydioxane and copolymers of these; ceramics such as alumina, zirconia and apatite; metallic materials such as stainless steel, cobalt alloy, titanium and titanium alloy; and inorganic materials such as calcium carbonate and calcium phosphate can be exemplified.

The form of the scaffold is not particularly limited, and is selected as appropriate according to the type of tissue to be regenerated, and the shape of the site to be regenerated. As examples of the form of the scaffold, porous, sheet, mesh, powder, etc. can be exemplified. In the case of the scaffold being a porous material, specific shapes of the porous material can include round pillar, polygonal pillar, flat plate, spherical, elliptical, etc.

Fifth Embodiment

The fifth embodiment of the present invention is a scaffold for tissue repair having glycosaminoglycan at the surface, and is a scaffold for tissue repair in which the aforementioned adhesive peptide is binding to the surface of the scaffold at the adhesive site possessed by the adhesive peptide, and the glycosaminoglycan is binding to the basic site possessed by the adhesive peptide. By using such a scaffold, similar effects to the effects explained for the second embodiment are obtained.

Sixth Embodiment

The sixth embodiment of the present invention is a scaffold for tissue repair including cell growth factor at the surface, and is a scaffold for tissue repair in which the aforementioned adhesive peptide is binding to the surface of the scaffold at the adhesive site possessed by the adhesive peptide, the cell growth factor is binding with glycosaminoglycan, and binding with the basic site possessed by the adhesive peptide via the glycosaminoglycan. By using such a scaffold, similar effects to the effects explained for the third embodiment are obtained.

Seventh Embodiment

The seventh embodiment of the present invention is a surface treatment method of a scaffold for tissue repair that brings the aforementioned adhesive peptide into contact with the surface of the scaffold for tissue repair. By bringing the adhesive peptide into contact with the surface of the scaffold for tissue repair, the adhesive peptide binds to the surface of the scaffold for tissue repair at the adhesive site. By doing this, it becomes possible to bind glycosaminoglycan at the basic site possessed by the adhesive peptide supported on the surface of the scaffold. The glycosaminoglycan binding to the basic site can further bind with various cell growth factors. For this reason, when binding glycosaminoglycan to the surface of the scaffold via the adhesive peptide and placing such a scaffold within the tissue to be repaired, depending on the type of tissue, it is possible to focus the cell growth factor present in the tissue at the periphery of the scaffold, thereby promoting repair of the tissue.

In addition, it is preferable to bind the cell growth factor to the glycosaminoglycan binding to the adhesive peptide supported on the surface of the scaffold in advance. When this is done, it is possible to control release of cell growth factor at the scaffold periphery by placing the scaffold within the tissue to be repaired, and thus the promoting effect on tissue repair can be further enhanced.

For the above reasons, the following processes (1) and (2), or processes (1), (2) and (3) are conducted on the surface of the scaffold.

(1) Process of bringing adhesive peptide into contact with surface of scaffold.

(2) Process of binding glycosaminoglycan to basic site possessed by adhesive peptide supported on the surface of the scaffold.

(3) Process of binding cell growth factor to the glycosaminoglycan bound to the adhesive peptide supported on the surface of the scaffold.

In addition, after performing the above-mentioned process (1), it is possible to conduct the following process (4) in place of processes (2) and (3). In the case of performing the process (4), the glycosaminoglycan in the complex of glycosaminoglycan and cell growth factor and the basic site possessed by the adhesive peptide will bind.

(4) Process of binding the complex of glycosaminoglycan and cell growth factor to the basic site possessed by the adhesive peptide supported on the surface of the scaffold.

By conducting processes (1) and (2) on the scaffold for tissue repair, it is possible to form the scaffold according to the fifth embodiment. In addition, it is possible to form the scaffold according to the sixth embodiment by conducting processes (1), (2) and (3), or processes (1) and (4) on the scaffold for tissue repair. Hereinafter, the above-mentioned steps (1) to (4) will be explained in order.

(Step (1))

The method of bringing the surface of the scaffold for tissue repair and the adhesive peptide into contact is not particularly limited. Upon bringing the surface of the scaffold for tissue repair and the adhesive peptide into contact, the adhesive peptide is usually used in the form of a solution due to uniform contact between the surface of the scaffold for tissue repair and the adhesive peptide being easy. As the method for bringing the solution of adhesive peptide into contact with the surface of the scaffold, methods like coating, spraying and immersing can be exemplified. Among these methods, immersing is preferable. This is because, although the scaffold may consist of a porous material, it possible to bring the adhesive peptide into contact with the inner surfaces of the pores possessed by the porous material.

The temperature and time upon bringing the adhesive peptide into contact with the surface of the scaffold are not particularly limited so long as binding of the adhesive peptide to the surface of the scaffold advances favorably. Typically, immersing is performed at 5 to 90° C., and preferably 20 to 70° C. In addition, the immersing time is preferably 0.1 to 48 hours, and more preferably 1 to 24 hours.

The amount used of adhesive peptide upon bringing the adhesive peptide into contact with the surface of the scaffold is preferably 0.1 to 50 mg/m$^2$, and more preferably 1.0 to 10 mg/m$^2$, relative to the surface area of the scaffold.

The concentration of the solution of adhesive peptide used during surface treatment is not particularly limited. Typically, the concentration of the solution of adhesive peptide is preferably 0.1 to 10 mg/mL, and more preferably 0.5 to 5 mg/mL.

After having brought the scaffold and solution of adhesive peptide into contact, Step (2) or (4) may be performed as is, or Step (2) or (4) may be performed after drying the scaffold.

(Step (2))

In Step (2), the glycosaminoglycan is bound to the basic site possessed by the adhesive peptide supported on the surface of the scaffold. In order to bind the glycosaminoglycan to the basic site possessed by the adhesive peptide supported on the surface of the scaffold, usually, the scaffold supporting the adhesive peptide on the surface and the solution of glycosaminoglycan are brought into contact. Although the glycosaminoglycan has a sulfonic group and carbonate group, which are acidic functional groups, these acidic groups may form salts such as a sodium salt or potassium salt in a solution of glycosaminoglycan.

Contacting between the scaffolding supporting the adhesive peptide on the surface and the solution of glycosaminoglycan is carried out by a similar method as the contacting between the scaffold and solution of adhesive peptide in Step (1). In the case of treating the scaffold supporting the adhesive peptide on the surface by immersing in a solution of glycosaminoglycan, the temperature during immersing and the time are not particularly limited so long as binding of the glycosaminoglycan to the adhesive peptide advances favorably. Typically, immersing is performed at 5 to 90° C., and preferably at 20 to 70° C. In addition, the immersing time is preferably 0.1 to 48 hours, and more preferably 1 to 24 hours.

The concentration of the solution of glycosaminoglycan used during surface treatment is not particularly limited. Typically, the concentration of the solution of glycosaminoglycan is preferably 0.1 to 10 mg/mL (in the case of heparin, 20 to 2000 units/mL as titer), and more preferably 0.5 to 5 mg/mL (in the case of heparin, 100 to 1000 units/mL as titer).

The amount used of glycosaminoglycan during surface treatment is not particularly limited, and is selected as appropriate so that a sufficient amount of glycosaminoglycan can bind to the adhesive peptide.

(Step (3))

In Step (3), cell growth factor is bound to the glycosaminoglycan binding at the basic site possessed by the adhesive peptide supported on the surface of the scaffold. In order to bind cell growth factor to the glycosaminoglycan binding at the basic site possessed by the adhesive peptide supported on the surface of the scaffold, usually, the scaffold supporting on the surface thereof the adhesive peptide to which the glycosaminoglycan is binding at the basic site and the solution of glycosaminoglycan are brought into contact. The contacting between the scaffold supporting on the surface the adhesive peptide to which glycosaminoglycan is binding at the basic site and the solution of glycosaminoglycan is performed by a similar method as the contacting between the scaffold and the solution of adhesive peptide in Step (1).

In the case of treating the scaffold supporting on the surface thereof the adhesive peptide to which glycosaminoglycan is binding at the basic site by immersing in a solution of cell growth factor, the temperature during immersing and the time are not particularly limited so long as binding of cell growth factor to the glycosaminoglycan advances favorably. Typically, immersing is performed at 5 to 70° C., and preferably 5 to 30° C. In addition, the immersing time is preferably 0.1 to 48 hours, and more preferably 1 to 24 hours.

The concentration of the solution of cell growth factor used during surface treatment is not particularly limited. Typically, the concentration of the solution of cell growth factor is preferably 1 to 1,000 µg/mL, and more preferably 10 to 500 µg/mL.

The amount used of cell growth factor during surface treatment is not particularly limited, and is selected as appropriate so that a sufficient amount of cell growth factor can bind to the glycosaminoglycan binding to the adhesive peptide.

(Step (4))

In Step (4), soon after Step (1), the scaffold supporting the adhesive peptide on the surface and the complex of glycosaminoglycan and cell growth factor are brought into contact, thereby binding the complex of glycosaminoglycan and cell growth factor to the basic site possessed by the adhesive peptide supported on the surface of the scaffold. The complex of glycosaminoglycan and cell growth factor is formed by mixing the glycosaminoglycan and cell growth factor in a solvent such as water.

Contacting between the scaffold supporting the adhesive peptide on the surface thereof and the complex of glycosaminoglycan and cell growth factor is preferably performed by immersing the scaffold supporting the adhesive peptide on the surface into a solution of the complex of glycosaminoglycan and cell growth factor. This immersing is performed similarly to Step (3).

Eighth Embodiment

The eighth embodiment of the present invention is a surface treatment method of the scaffold for tissue repair that brings the complex consisting of the adhesive peptide and glycosaminoglycan according to the second embodiment into contact with the scaffold for tissue repair. The contacting between the complex according to the second embodiment and the scaffold is performed similarly to Step (1) explained for the surface treatment method according to the seventh embodiment, using the solution of complex according to the second embodiment.

After bringing the complex according to the second embodiment and the scaffold into contact, the scaffold supporting the complex according to the second embodiment on the surface and the cell growth factor may be brought into contact as necessary. By doing this, the cell growth factor binds to the glycosaminoglycan in the complex according to the second embodiment supported on the surface of the scaffold.

Ninth Embodiment

The ninth embodiment of the present invention is a surface treatment method of a scaffold for tissue repair that brings the complex consisting of the adhesive peptide, glycosaminoglycan and cell growth factor according to the third embodiment into contact with the scaffold for tissue repair. The contacting between the complex according to the third embodiment and the scaffold is performed similarly to Step (3) explained for the surface treatment method according to the seventh embodiment, using the solution of complex according to the third embodiment.

Tenth Embodiment

The tenth embodiment of the present invention is a surface treatment solution of a scaffold for tissue repair containing the aforementioned adhesive peptide. The type of solvent contained in the surface treatment solution according to the tenth embodiment is not particularly limited in a scope that does not inhibit the objects of the present invention, so long as being able to dissolve the adhesive peptide. Due to not having a negative influence on the solubility of the adhesive peptide, on the tissue to be repaired using the scaffold, etc., usually, water is used as the solvent contained in the surface treatment solution.

The preparation method of the surface treatment solution is not particularly limited. In the case of the adhesive peptide being in the state of a solution, the surface treatment solution is obtained by diluting or concentrating the solution containing the adhesive peptide so that the concentration of the adhesive peptide becomes the desired concentration. In the case of the adhesive peptide being powderized by a method such as freeze drying, the surface treatment solution is obtained by mixing the powder of adhesive peptide and the solvent such as water at a predetermined ratio, and dissolving the adhesive peptide in solvent.

The concentration of adhesive peptide in the surface treatment solution is not particularly limited. The preferred concentration of adhesive peptide in the surface treatment solution is similar to the solution of adhesive peptide used in Step (1) explained for the surface treatment method according to the seventh embodiment.

The surface treatment solution according to the tenth embodiment may contain various additives that will not bind with the adhesive site and basic site possessed by the adhesive peptide, in a range not inhibiting the objects of the present invention. As additives blended into the surface treatment solution, a pH adjuster, osmoregulating agent, surfactant, viscosity adjuster, stabilizer, pigment, fragrance, antioxidant, antiseptic, anti-mold agent, UV absorbing agent, etc. can be exemplified. These additives are added to the surface treatment solution according to the amounts at which these additives are usually blended relative to various chemicals.

Eleventh Embodiment

The eleventh embodiment of the present invention is a set of treatment solutions for surface treatment of a scaffold for tissue repair including the surface treatment solution containing the adhesive peptide according to the tenth embodiment and the surface treatment solution containing glycosaminoglycan. The type of solvent contained in the surface treatment solution containing glycosaminoglycan is not particularly limited in a range not inhibiting the objects of the present invention, so long as being able to dissolve the glycosaminoglycan. Due to not having a negative influence on the solubility of glycosaminoglycan, on the tissue to be treated using the scaffold, etc., usually, water is used as the solvent contained in the surface treatment solution containing glycosaminoglycan.

The concentration of glycosaminoglycan in the surface treatment solution containing glycosaminoglycan is not particularly limited. The preferred concentration of glycosaminoglycan in the surface treatment solution is similar to the solution of glycosaminoglycan used in Step (2) explained for the surface treatment method according to the seventh embodiment. The surface treatment solution containing glycosaminoglycan may contain various additives similarly to the surface treatment solution containing adhesive peptide.

The set of treatment solutions for surface treatment of the scaffold for tissue repair according to the eleventh embodiment may further include a surface treatment solution containing cell growth factor. The preferred concentration of cell growth factor in the surface treatment solution is similar to the solution of cell growth factor used in Step (3) explained for the surface treatment method according to the seventh embodiment. The surface treatment solution containing cell growth factor may include various additives similarly to the surface treatment solution containing adhesive peptide.

Twelfth Embodiment

The twelfth embodiment of the present invention is a surface treatment solution containing the complex of the adhesive peptide and glycosaminoglycan according to the second embodiment. The type of solvent contained in the surface treatment solution according to the twelfth embodiment is not particularly limited in a range not inhibiting the objects of the present invention, so long as being able to dissolve the complex. Due to not having a negative influence on the solubility of the complex, on the tissue to be repaired using the scaffold, etc., usually, water is used as the solvent contained in the surface treatment solution.

The preparation method of the surface treatment solution containing the complex according to the second embodiment is similar to the preparation method of the surface treatment solution according to the tenth embodiment. The concentration of complex in the surface treatment solution is not particularly limited. For the concentration of complex in the surface treatment solution, it is preferable for the concentration of adhesive peptide included in the complex in the surface treatment solution to be similar to the ideal concentration of the solution of adhesive peptide used in Step (1) explained for the surface treatment method according to the seventh embodiment. The surface treatment solution containing the complex of adhesive peptide and glycosaminoglycan may include various additives similarly to the surface treatment solution according to the tenth embodiment.

Thirteenth Embodiment

The thirteenth embodiment of the present invention is a set of treatment solutions for surface treatment of a scaffold for tissue repair, including the surface treatment solution containing the complex of adhesive peptide and glycosaminoglycan, and the surface treatment solution containing cell growth factor. The surface treatment solution containing cell growth factor is similar to that explained for the eleventh embodiment.

Fourteenth Embodiment

The fourteenth embodiment of the present invention is a surface treatment solution containing a complex of the adhesive peptide, glycosaminoglycan and cell growth factor according to the third embodiment. The type of solvent contained in the surface treatment solution according to the fourteenth embodiment is not particularly limited in a range not inhibiting the objects of the present invention, so long as being able to dissolve the complex. Due to not having a negative influence on the solubility of complex, on the tissue to be repaired using the scaffold, etc., usually, water is used as the solvent contained in the surface treatment solution.

The preparation method of the surface treatment solution containing the complex according to the third embodiment is similar to the preparation method of the surface treatment solution according to the tenth embodiment. The concentration of the complex in the surface treatment solution is not particularly limited. For the concentration of complex in the surface treatment solution, it is preferable for the concentration of adhesive peptide contained in the complex in the surface treatment solution to be the same as the ideal concentration of the solution of adhesive peptide used in Step (1) explained for the surface treatment method according to the seventh embodiment. The surface treatment solution containing a complex of the adhesive peptide, glycosaminoglycan and cell growth factor may include various additives, similarly to the surface treatment solution according to the tenth embodiment.

EXAMPLES

Although the present invention will be explained by way of examples hereinafter, the scope of the present invention is not to be limited to these examples.

Example 1

According to the Fmoc solid-phase synthesis method, an adhesive peptide was synthesized consisting of the amino acid sequence of the SEQ ID NO. (2) below, in which the sequence of nine residues from the C terminus is the amino acid sequence of SEQ ID NO. (1) below.

Ala-Lys-Pro-Ser-Tyr-Hyp-Thr-Xaa-Lys     (1)

Lys-Lys-Lys-Lys-Lys-Gly-Gly-Gly-Ala-Lys-Pro-Ser-Tyr-Hyp-Thr-Xaa-Lys     (2)

(In SEQ ID NOS. (1) and (2), Xaa is a residue of L-dopa.)

After purifying the crude adhesive peptide obtained by reverse phase HPLC, the molecular weight of the purified adhesive peptide was measured by MALDI-TOF/MS. The molecular weight of the peptide measured by MALDI-TOF/MS was 2011.7, and was substantially equal to the molecular weight of 2011.3 upon calculation of the adhesive peptide consisting of the amino acid sequence of SEQ ID NO. (3).

Example 2

An aqueous solution of adhesive peptide with a concentration of 1.0 mg/mL was prepared by dissolving the adhesive peptide obtained in Example 1 in distilled water. The substrate of the scaffold for tissue repair of columnar type having a diameter of 5 mm and height of 2 mm consisting of a porous body (approx. 70% of volume of porous body occupied by volume of micropores) of α-TCP (α-tricalcium phosphate) was immersed in 0.1 mL of an aqueous solution of adhesive peptide for 24 hours at 50° C. to bind the adhesive peptide to the surface of the substrate. Subsequently, the substrate was removed from the aqueous solution of adhesive peptide, and the substrate was dried after washing with 20 mL of distilled water. Upon analyzing the surface of the dried substrate by way of X-ray photoelectron spectroscopy (XPS), the peak of N1s resulting from the nitrogen atoms contained in the peptide was confirmed.

Example 3

Other than changing the concentration of the aqueous solution of adhesive peptide from 1.0 mg/mL to 2.0 mg/mL, the substrate of the scaffold for tissue repair was treated with the adhesive peptide aqueous solution similarly to Example 2. Upon analyzing the dried surface of the substrate of the scaffold for tissue repair by way of XPS similarly to Example 2, the peak of N1s resulting from the nitrogen atoms contained in the peptide was confirmed.

Example 4

The substrate of the scaffold for tissue repair treated by the adhesive peptide obtained in Example 2 was immersed in Novo heparin (10,000 units/10 mL, manufactured by Mochida Pharmaceutical Co., Ltd.) at room temperature for 8 hours to bind the heparin at the basic site of the adhesive peptide supported on the substrate of the scaffold. Subsequently, the substrate was removed from the Novo heparin, and the substrate was dried after washing with 20 mL of distilled water.

Example 5

Other than changing the substrate of the scaffold for tissue repair treatment by the adhesive peptide obtained in Example 2 to the substrate obtained in Example 3, the substrate of the scaffold for tissue repair was treated with Novo heparin similarly to Example 4.

Example 6

An aqueous solution of cell growth factor was prepared using a glass vial containing a freeze-dried product of human recombinant FGF as the cell growth factor, which is associated with Fiblast (registered trademark) spray 250 (manufactured by Kaken Pharmaceutical CO., Ltd.), and the aqueous solution. More specifically, an aqueous solution of cell growth factor with a concentration of 100 μg/mL was prepared by adding the solution to the glass vial to dissolve the freeze-dried product of human recombinant FGF in the solution. The cell growth factor was bound to the heparin binding to the adhesive peptide at the surface of the substrate by immersing the substrate of the scaffold for tissue repair treated with heparin and adhesive peptide obtained in Example 4 into 0.5 mL of the prepared aqueous solution of cell growth factor. Subsequently, the substrate was extracted from the aqueous solution of cell growth factor, and the substrate was dried after washing with 20 mL of distilled water. Upon analyzing the surface of the substrate prior to being treated using cell growth factor, and the surface of the substrate after treatment by way of XPS, it was confirmed that the intensity of the peaks of C2s were remarkably enhanced by treatment using cell growth factor. This is considered to be due to the increase in the number of carbon atoms at the substrate surface due to the cell growth factor binding to the heparin that binds to the adhesive peptide of the substrate surface.

Example 7

Other than changing the substrate of the scaffold for tissue repair treated with heparin and adhesive peptide obtained in Example 4 with the substrate obtained in Example 5, the substrate of the scaffold for tissue repair was treated with the aqueous solution of cell growth factor similarly to Example 6. Upon analyzing the surface of the substrate prior to being treated using cell growth factor, and the surface of the substrate after treatment by way of XPS, it was confirmed that the intensity of the peak of C2s was remarkably enhanced by treatment using cell growth factor.

Example 8, Example 9 and Comparative Example 1

After implanting the scaffold for tissue repair to which cell growth factor is binding to the heparin binding to the adhesive peptide of the substrate surface, or scaffold for tissue repair not surface treated, under the skin of 6-week old male ICR mouse, the tissue in the vicinity of the scaffold was observed 7 days after implantation. In Example 8, the scaffold for tissue repair obtained in Example 6 was used. In Example 9, the scaffold for tissue repair obtained in Example 7 was obtained. In Comparative Example 1, a scaffold for tissue repair that is not surface treated was used. Images of the subdermal tissue of ICR mouse 7 days after scaffold implantation of Example 8, Example 9 and Comparative Example 1 are shown as FIG. 1 (Example 8), FIG. 2 (Example 9) and FIG. 3 (Comparative Example 1).

Figure 1:
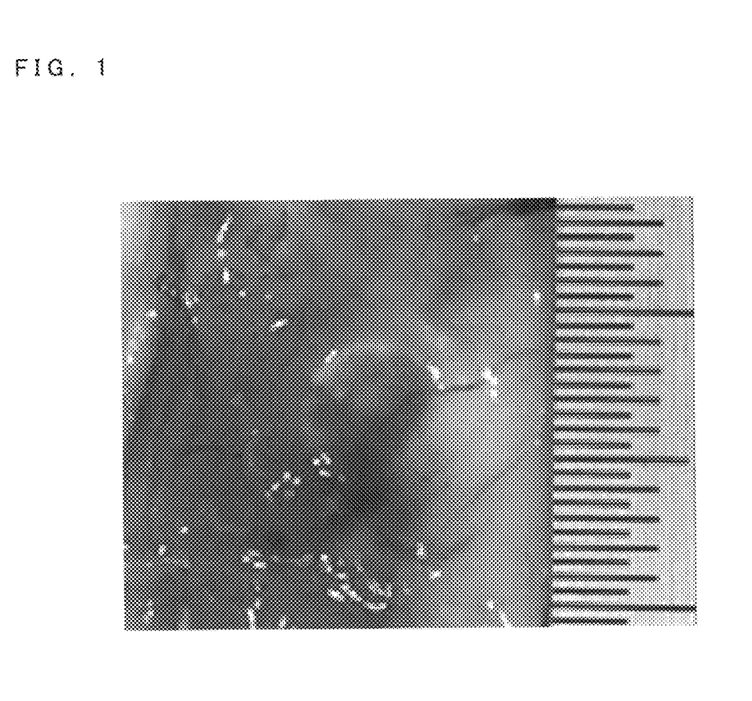
FIG. 1 is a view showing an image of the subcutaneous tissue of ICR mouse 7 days after scaffold implantation, photographed for Example 8.
Figure 2:
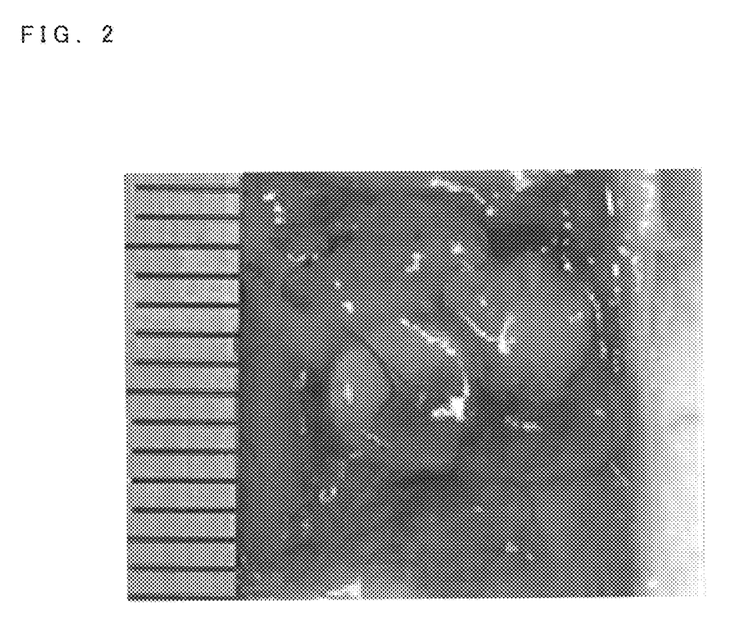
FIG. 2 is a view showing an image of the subcutaneous tissue of ICR mouse 7 days after scaffold implantation, photographed for Example 9.
Figure 3:
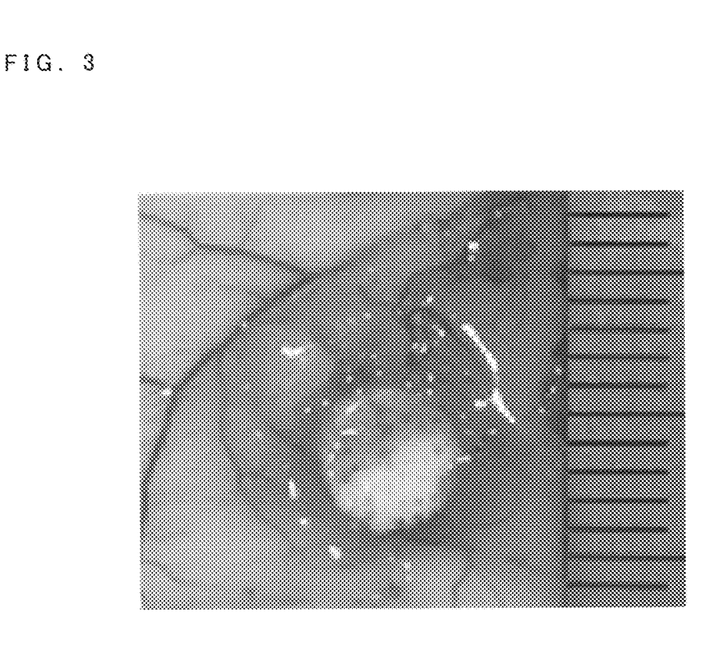
FIG. 3 is a view showing an image of the subcutaneous tissue of ICR mouse 7 days after scaffold implantation, photographed for Comparative Example 1.

According to FIGS. 1 and 2, in the case of using a scaffold for tissue repair in which cell growth factor is binding with the heparin binding to the adhesive peptide of the substrate surface, it is found that the angiogenesis of subcutaneous tissue of the ICR mouse progresses favorably. On the other hand, according to FIG. 3, in the case of using the scaffold for tissue repair not surface treated, it is found that the rate of angiogenesis was slow.

Reference Examples 1 to 4

Figure 6:
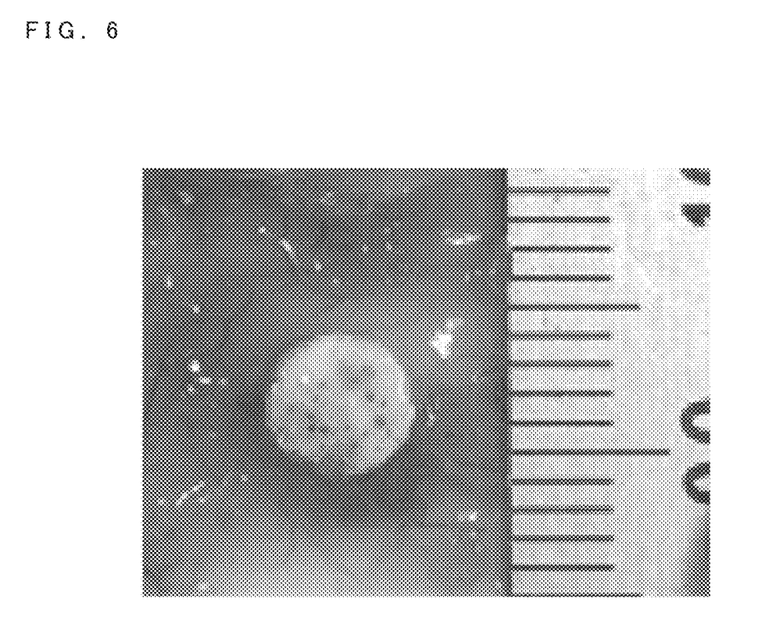
FIG. 6 is a view showing an image of the subcutaneous tissue of ICR mouse 7 days after scaffold implantation, photographed for Reference Example 3.
Figure 7:
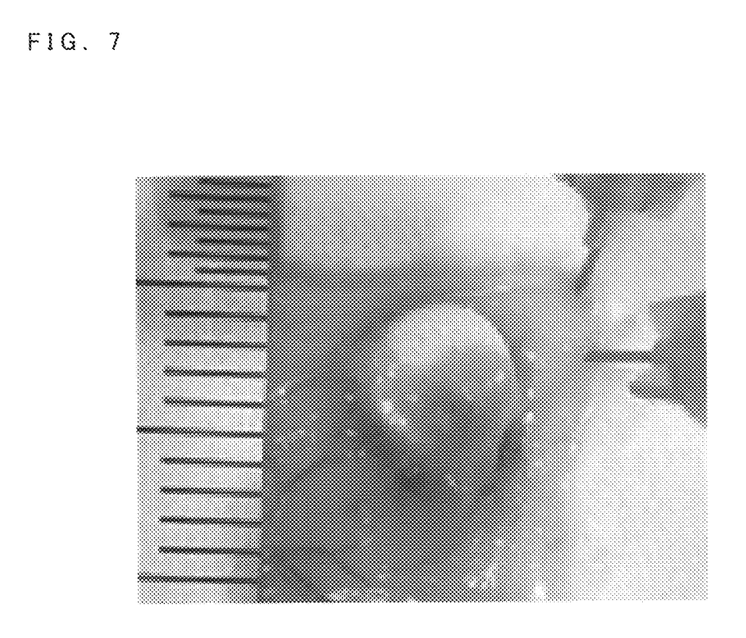
FIG. 7 is a view showing an image of the subcutaneous tissue of ICR mouse 7 days after scaffold implantation, photographed for Reference Example 4.

Other than using a scaffold for tissue repair in which the adhesive peptide is binding to the substrate surface, or a scaffold for tissue repair in which heparin is binding to the adhesive peptide of the substrate surface, the subcutaneous tissue of ICR mouse 7 days after scaffold implantation was observed similarly to Example 8. In Reference Example 1, the scaffold for tissue repair obtained in Example 2 was used. In Reference Example 2, the scaffold for tissue repair obtained in Example 3 was used. In Reference Example 3, the scaffold for tissue repair obtained in Example 4 was used. In Reference Example 4, the scaffold for tissue repair obtained in Example 5 was used. Images of the subcutaneous tissue of ICR mouse 7 days after scaffold implantation for Reference Examples 1 to 4 are shown as FIG. 4 (Reference Example 1), FIG. 5 (Reference Example 2), FIG. 6 (Reference Example 3) and FIG. 7 (Reference Example 4).

Figure 4:
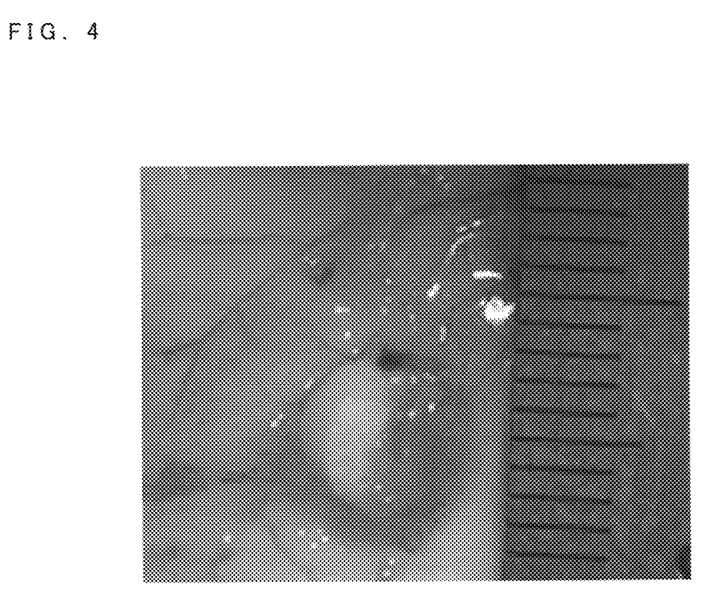
FIG. 4 is a view showing an image of the subcutaneous tissue of ICR mouse 7 days after scaffold implantation, photographed for Reference Example 1.
Figure 5:
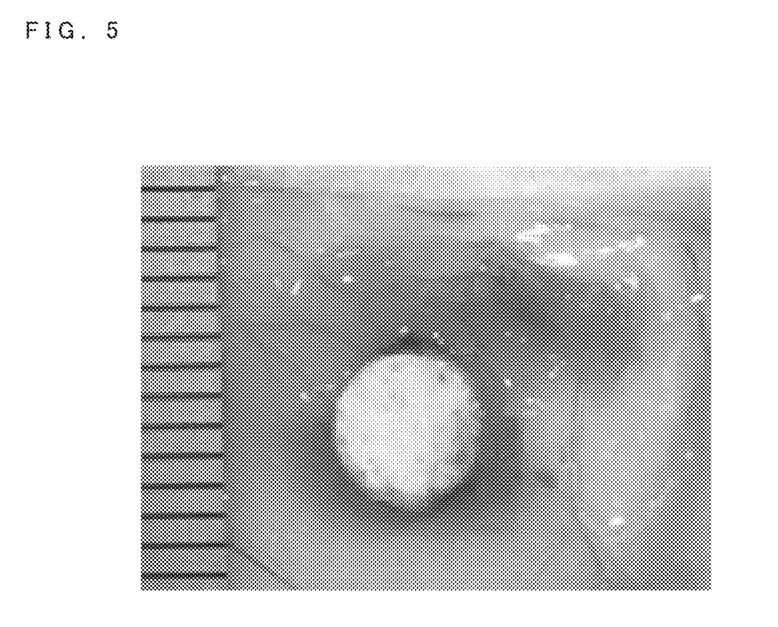
FIG. 5 is a view showing an image of the subcutaneous tissue of ICR mouse 7 days after scaffold implantation, photographed for Reference Example 2.

According to FIGS. 4 and 5, in the case of using a scaffold for tissue repair that was surface treated using only the adhesive peptide, it is found that the rate of angiogenesis was slow in the subcutaneous tissue of ICR mouse. According to FIGS. 5 and 6, also in the case of using a scaffold for tissue repair that was surface treated with adhesive peptide and heparin, it is found that the rate of angiogenesis was slow in the subcutaneous tissue of ICR mouse.

Example 10

Following Example 8, histological evaluation was performed for the subcutaneous tissue of ICR mouse 28 days after implantation of the scaffold obtained in Example 6

Figure 8:
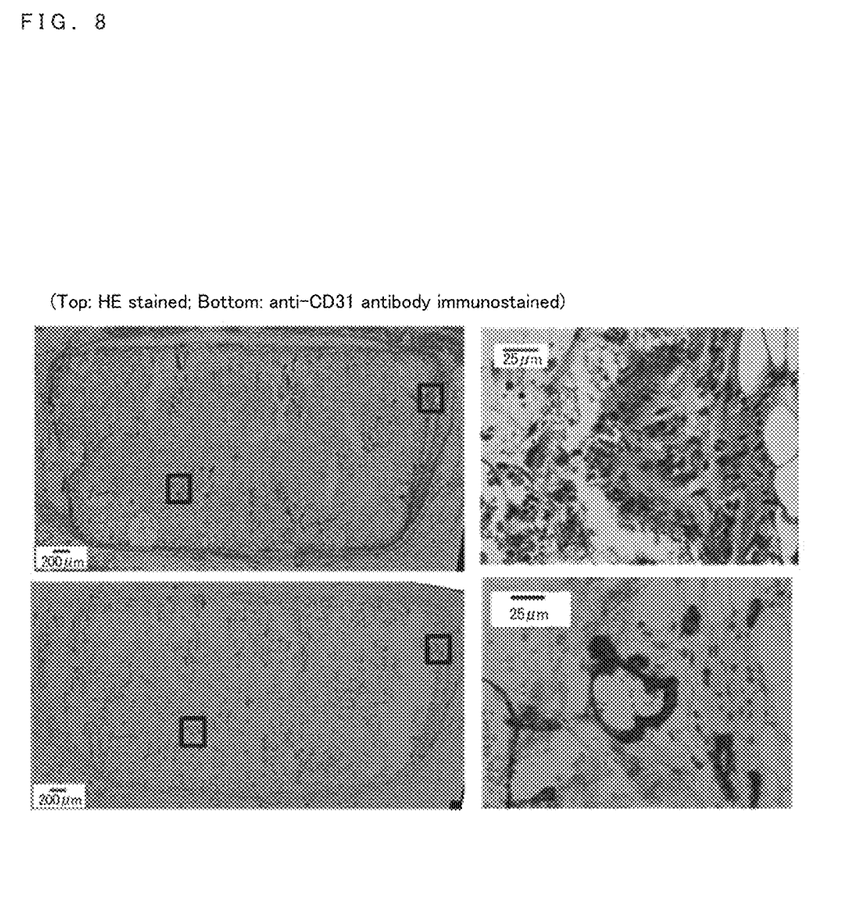
FIG. 8 is a view showing images after HE staining and anti-CD31 antibody immunostaining of the subcutaneous tissue of ICR mouse 28 days after scaffold implantation, photographed for Example 10.

The histological evaluation was performed by HE staining and anti-CD31 antibody immunostaining. Images of cross-sections of subcutaneous tissue after HE staining and anti-CD31 antibody immunostaining are shown in FIG. 8. In the images shown in FIG. 8, many invasive cells and vascular structures were recognized. In other words, by using a scaffold that was surface treated with the adhesive peptide, heparin and cell growth factor, the repair of subcutaneous tissue of ICR mouse advances favorably.

Example 11 and Comparative Example 2

(Bone Regeneration Trial of Mouse Skull)

Powder of α-TCP (α-tricalcium phosphate) was surface treated using the adhesive peptide obtained in Example 1 and heparin. More specifically, 28.7 mg of powder of α-TCP (α-tricalcium phosphate) was immersed in 0.1 mL of an aqueous solution of the adhesive peptide obtained in Example 1 with a concentration of 1.0 mg/mL at 50° C. for 24 hours in the dark, then air dried overnight in an incubator. The obtained peptide-modified α-TCP powder was immersed for 8 hours at room temperature in 0.1 mL of Novo heparin (10,000 units/10 mL, manufactured by Mochida Pharmaceutical Co., Ltd.), and subjected to air drying in an incubator to obtain powder of surface treated α-TCP. In Example 11, the obtained surface treated α-TCP powder was used as the scaffold. In Comparative Example 2, untreated α-TCP powder was used as the scaffold.

A bone defect with a diameter of 4 mm and depth of 0.3 mm was formed using a trephine bar in the skull of the mouse. The bone defect thus formed was filled with powder-form scaffold. After filling of scaffold, the bone defect site was covered with ePTFE film. Four weeks after scaffold filling, the bone defect was imaged by X-ray CT. The X-ray CT image of Example 11 is shown in FIG. 9, and the X-ray CT image of Comparative Example 2 is shown in FIG. 10.

Figure 9:
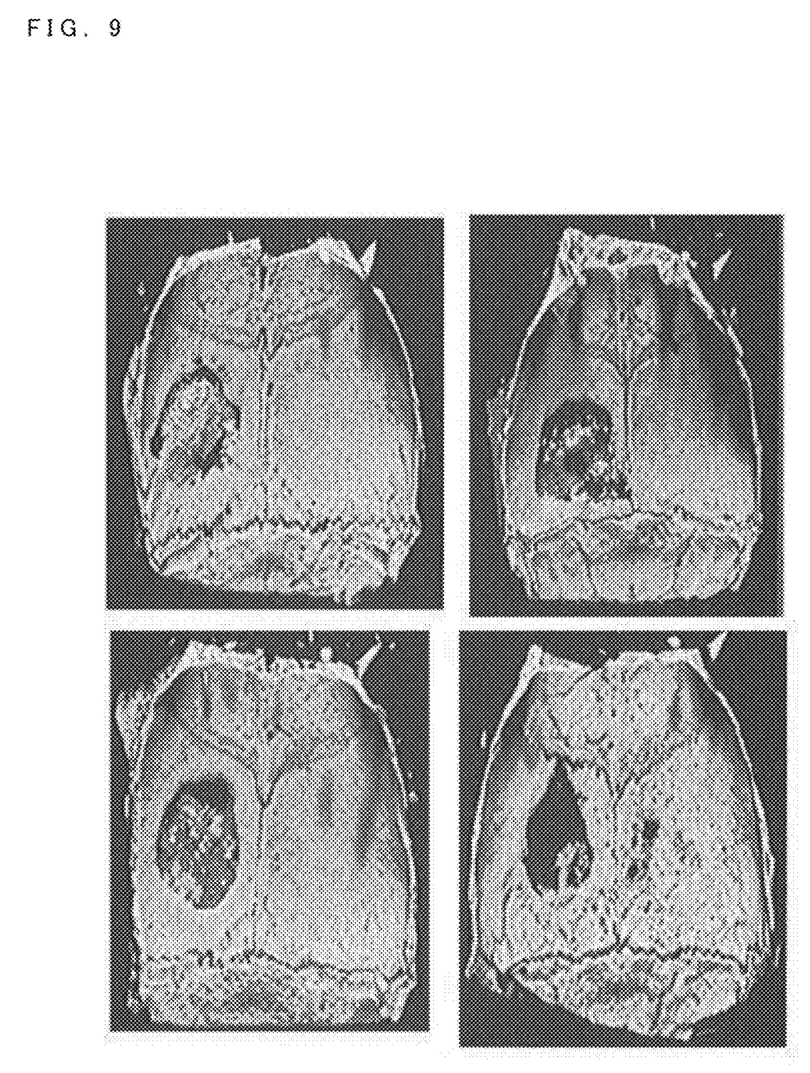
FIG. 9 is a view showing an X-ray CT image of a bone defect in a mouse 4 weeks after scaffold filling, photographed for Example 11.
Figure 10:
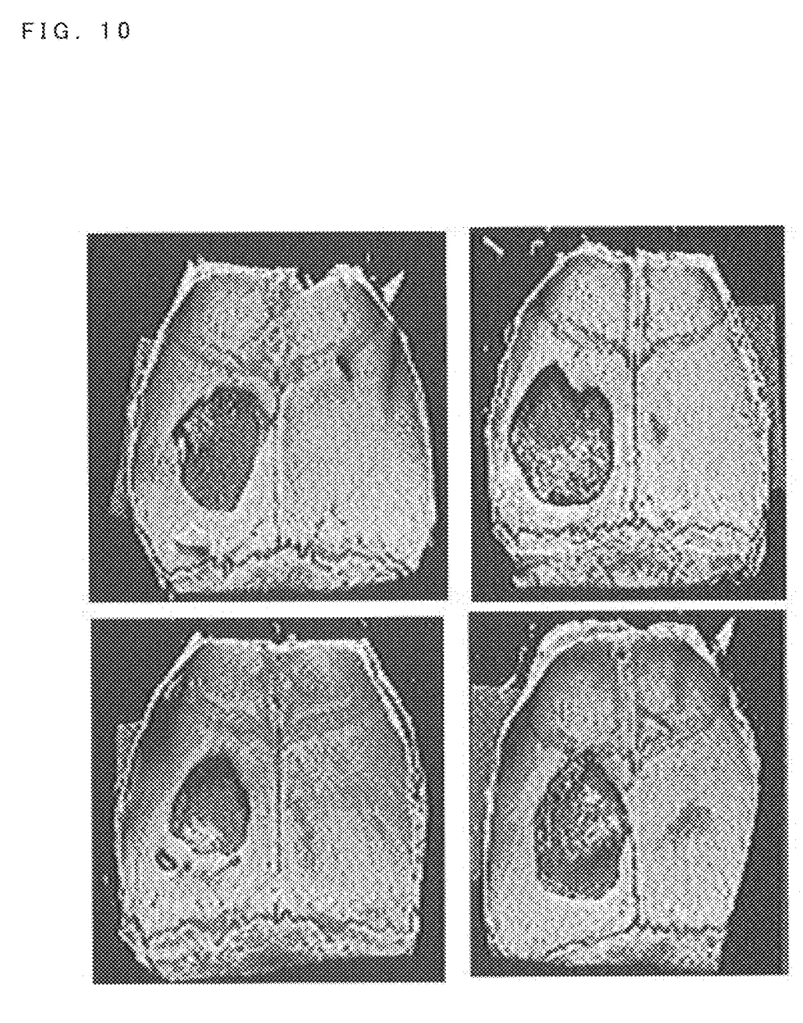
FIG. 10 is a view showing an X-ray CT image of a bone defect in a mouse 4 weeks after scaffold filling, photographed for Comparative Example 2.

According to comparison of FIGS. 9 and 10, it is found that whitening in the bone defect in the image advanced more for FIG. 9. In other words, bone regeneration progressed more in Example 11 than Comparative Example 2. In the case of using a scaffold surface treated with the adhesive peptide and heparin, it is considered that cell growth factor inherent to the mouse cranium is captured at the surface of the scaffold, whereby bone regeneration is promoted.

(Sequence Table)

We claim:

1. A complex of peptide and glycosaminoglycan, wherein the peptide comprises, in the amino acid sequence thereof, an adhesive site consisting of residues of amino acids including a 2,3-dihydroxyphenyl group or 3,4-dihydroxyphenyl group, and a basic site including three or more consecutive basic amino acid residues;

wherein the adhesive site and the basic site bind via a spacer site, and wherein the glycosaminoglycan is binding at the basic site.

2. The complex according to claim 1, wherein a sequence of nine resides from the C terminus of the peptide is an amino acid sequence represented by SEQ ID NO 1.

3. A complex of the complex according to claim 1 and a cell growth factor,
   wherein the cell growth factor is binding with the glycosaminoglycan.

4. A scaffold for tissue repair, wherein the complex according to claim 1 is binding to the surface thereof at the adhesive site.

5. A scaffold for tissue repair, wherein a complex of the complex according to claim 1 and a cell growth factor are binding to a surface of the scaffold at the adhesive site.

6. A treatment solution for surface treatment of a scaffold for tissue repair, comprising the complex according to claim 1.

7. A set of treatment solutions for surface treatment of a scaffold for tissue repair, comprising the treatment solution according to claim 6 and a treatment solution containing cell growth factor.

8. A treatment solution for surface treatment of a scaffold for tissue repair, comprising a complex of the complex according to claim 1 and a cell growth factor.

* * * * *

```
SEQUENCE LISTING

<160> NUMBER OF SEQ ID NOS: 2

<210> SEQ ID NO 1
<211> LENGTH: 9
<212> TYPE: PRT
<213> ORGANISM: Mytilus galloprovincialis
<220> FEATURE:
<221> NAME/KEY: MISC_FEATURE
<222> LOCATION: (6)..(6)
<223> OTHER INFORMATION: Xaa in position 6 is Hyp
<220> FEATURE:
<221> NAME/KEY: MISC_FEATURE
<222> LOCATION: (8)..(8)
<223> OTHER INFORMATION: Xaa in position 8 is 3-(3,4-dihydroxyphenyl)-
      L-alanine (L-DOPA)

<400> SEQUENCE: 1

Ala Lys Pro Ser Tyr Xaa Thr Xaa Lys
1               5

<210> SEQ ID NO 2
<211> LENGTH: 17
<212> TYPE: PRT
<213> ORGANISM: ArtificIal Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Xaa in position 14 is Hyp
<220> FEATURE:
<221> NAME/KEY: MISC_FEATURE
<222> LOCATION: (16)..(16)
<223> OTHER INFORMATION: Xaa in position 16 is 3-(3,4-dihydroxyphenyl)-
      L-alanine (L-DOPA)

<400> SEQUENCE: 2

Lys Lys Lys Lys Lys Gly Gly Gly Ala Lys Pro Ser Tyr Xaa Thr Xaa
1               5                   10                  15

Lys
```